US00RE35458E

United States Patent [19]

Azuara

[11] E Patent Number: Re. 35,458

[45] Reissued Date of Patent: Feb. 18, 1997

[54] PROCESS TO OBTAIN NEW MIXED COPPER AMINOACIDATE COMPLEXES FROM PHENYLATE PHENATHROLINES TO BE USED AS ANTICANCERIGENIC AGENTS

[75] Inventor: Lena R. Azuara, Villa de Cortes, Mexico

[73] Assignee: Universidad Nacional Autonoma De Mexica (UNAM), Mexico

[21] Appl. No.: 230,816

[22] Filed: Apr. 21, 1994

Related U.S. Patent Documents

Reissue of:

[64] Patent No.: 5,107,005
Issued: Apr. 21, 1992
Appl. No.: 628,843
Filed: Dec. 11, 1990

[30] Foreign Application Priority Data

Dec. 20, 1989 [MX] Mexico ..... 18802

[51] Int. Cl.[6] ..... C07F 1/08

[52] U.S. Cl. ..... 556/116; 556/110; 546/88

[58] Field of Search ..... 556/116, 110; 546/88; 514/499, 184, 81

[56] References Cited

U.S. PATENT DOCUMENTS

| | | | |
|---|---|---|---|
| 4,657,928 | 4/1987 | Sorenson | 514/499 |
| 4,965,384 | 10/1990 | Cliffton et al. | 556/110 |
| 5,041,573 | 8/1991 | Hasegana et al. | 556/116 X |
| 5,164,367 | 11/1992 | Pickart | 514/6 |

OTHER PUBLICATIONS

W. L. Kwik et al., Complexes of (2,2'-Bipyridyl) Copper(II) and (1,10-Phenanthroline) Copper(II) with Some Amino Acids, Org. Nucl. Chem., vol. 42, pp. 303-313 (1980).

W. L. Kwik et al., 2,9-Dimethyl-1,10-phenanthroline Copper(I) Complexes with Some Sulphur-containing Amino Acids, J. Chem. Soc. Dalton Trans. (1983).

*Primary Examiner*—Josè G. Dees
*Assistant Examiner*—Rosalynd A. Williams
*Attorney, Agent, or Firm*—Finnegan, Henderson, Farabow, Garrett & Dunner

[57] ABSTRACT

This invention refers to a process to obtain new mixed copper aminoacidates complexes from phenanthrolines of an aromatic type to be used as anticancerigenic agents preferably with a therapeutic use for the treatment of liquid and solid cancerigenic tumors such as leukemia. The complexes obtained are of the [Cu (N-N) (N-O)]± $NO_3$ type in which the N-N ligand corresponds to 4, 7-diphenyl-1, 10 phenanthroline and the N-O ligand preferably corresponds to one of the aminoacidates such as glycinate, alaninate, isoleucinate, leucinate, serinate and valinate. The process is characterized because it includes the following steps: making an aqueous solution based on an aliphatic alcohol and 4,7-diphenyl-1, 10 phehanthrolin react with a copper complex preferably Cu $NO_3$ $5H_2O$ at room temperature, and immediately after making the obtained product react in an aqueous aminoacidate solution adjusting a slightly alkaline pH.

7 Claims, No Drawings

PROCESS TO OBTAIN NEW MIXED COPPER AMINOACIDATE COMPLEXES FROM PHENYLATE PHENATHROLINES TO BE USED AS ANTICANCERIGENIC AGENTS

Matter enclosed in heavy brackets [ ] appears in the original patent but forms no part of this reissue specification; matter printed in italics indicates the additions made by reissue.

BACKGROUND OF THE INVENTION

A type of drug for which a correlation between biological activity and structure has been found is the metal chelating agent such as iron, ruthenium, cobalt, manganese, zinc and copper (Dwyer, F. F. et al. Nature. 179, (1956), 425–426). Chelating agents can be designed to inactive bacteria, viruses and fungi by capturing the metallic ions necessary for the metabolism of these microorganisms. They can also be supplied with metallic ions that prove toxic to them.

Studies related to the composition of physiological fluids have shown that the metallic ions present in these systems are largely found in the form of mixed complexes. Here the term mixed complex must be understood to mean all those coordination complexes with two or three chelate type ligands that are different one from the other, excluding the solvent of the chelate ligand category.

Sigel and colleagues (Sigel, H. et al., JACS 99:13 (1976), 4489–4496) have shown that in many cases the enzymatic action depends on an elementary process in which an enzyme-substrate complex is generated that presents characteristics analogous to those of a mixed complex.

Certain metallic chelates supplied in small concentrations are active agents against some bacteria, fungi, viruses and some tumorous cells.

It is well known, for instance, that Staphylococcus pyrogenes, which has been detected in infected wounds and has proved to be highly resistant to the action of many standard antibiotics, perishes in the presence of the iron (tetramethyl 1, 1, 10-phenanthroline)$_3$ (acetylacetonate)+ and ruthenium (tetramethyl-1, 10 phenanthroline)$_2$(acetylacetonate)+ complexes. The biological activity of these saturated chelate complexes is principally due to the stereochemistry of the complex as a whole, the ionic nature of the coordinating sphere, the nature of the coordination center, the lyophilicity of the ligands, the redox potentials of the complexes, the thermodynamic stability and kinetic of the metallic chelates.

Volpir and colleagues have studied the catalytic activity of the Co (II) and Cu (II) complexes with orthophenanthrolines in the oxidation processes of the NADH, $Q_4$ $H_2$ (quinone), $Q_9$ $H_2$ (ubiquinone) and cytochrome C substrates.

The [Cu(2,9-dimethyl-1,1-phenanthroline)]$\pm Cl_2$ complex is an effective inhibitor of the growth of the plasmodium Microplasmacillisepticum, a very dangerous pathogenic microorganism that induces pulmonary diseases in man.

D. R. Williams has calculated the distribution percentages of the Cu(II), Fe(II), Mn(II) and Zn(II) ions with low weight ligands, the predominant molecules in human blood plasma; Cu (hys) (Cys); (ulhys)$_2$ and Cu (hys) (CysH)$^+$ are among the most abundant complexes. Mention is made in the literature of studies on the absorption of the Mn (gly)$_2$ and Mn(L-ala)$_2$ chelate complexes through the intestinal wall in dogs.

Kwik and colleagues have reported the synthesis of mixed complexes with the general formula [Cu(phenanthroline) (aminoacidate)]n$H_2O$, [Cu (bipyridine) (aminoacidate)]n $H_2O$, [Cu (phenanthroline) (aminoacidate) (Cl, $O_2$, $SO_4$)] n$H_2O$ where the aminoacidate is the glycinate, alaninate, valinate, tyrosinate, serinate, aspartate or glutamate ion.

Where the general synthesis method consists of preparing an aqueous solution with 5 mmol of $CuSO_4$. $5H_2O$ in 20 ml of distilled water which is slowly added to an ethanolic solution with 8 mmoles of o-phenanthroline in 20 ml of ethanol, a solution blue in color is immediately formed. The mixture is magnetically shaken and at the same time a solution of 10 ml of HC1 0.1 M containing one of the aminoacidates is added slowly, immediately followed by a solution of ammonium hydroxide 1 M until the solution becomes clear. The mixture that has been thus prepared is heated and shaken for 30 minutes; the heating process is continued until the volume is reduced by half, the product obtained is cooled in ice until a solid is formed, it is filtered, washed in small pieces in cold water and is then in ethanol and is finally vacuum dried.

The applicant has developed a process to obtain new chelates by means of the synthesis and characterization of mixed chelate complexes of ions Mn (II), Fe (II), Ni (II), Co (II, III), Cu (II) Zn (II) and Ru (II) with ligands of the N-N (phenanthrolines and bipyridines), O-O (acethylacetonate and salicilaldehydate ions) and N-O (aminocidate ions) type. These mixed chelate complexes have some type of potential biological activity.

With the ion Cu (II) in particular 6 new mixed complexes of the [Cu (N-N) (N-O)]$^{\pm}$ $NO_3$ type have been isolated.

SUMMARY OF THE INVENTION

This invention refers to a process to obtain new mixed copper aminoacidate complexes from phenylate phenanthrolines of an aromatic type with anticancerigenic properties, with the formula [Cu (N-N) (N-O)]$^{35}$ $NO_3$, in which the N-N ligand (diimine) corresponds to a group of 4,7-diphenyl-1, 10-phenanthroline and the N-O ligand is an aminoacidate that corresponds principally to the following ions: glycinate, alaninate, isolecinate, leucinate, serinate and valinate; and is characterized because it comprises the steps for preparing an aqueous solution based on a copper compound, preferably Cu $(NO_3)_2$, $5H_2O$ at a ratio of 30%–35% copper weight/solution; prepare an aqueo-ethanolic solution with a diimine compound at a ratio of 50%–55% diimine weight/solution; make the aqueous solutions react in a reactor at room temperature; stabilize the copper complex obtained (mono-diimine nitrate) with a regulating agent maintaining an acid pH of between 5 and 7; add to the complex obtained an aqueous solution of 10%–15% in weight of an aminoacidate (N-O) keeping the reaction slightly alkaline to obtain copper aminoacidate aromatic complexes with anticancerigenic properties with the formula:

1) [Cu (4,7diphenyl-1,10-phenanthroline) (alaninate)]$^{\pm}NO_3$
2) [Cu (4,7diphenyl-1,10-phenanthroline) (glycinate)]$^{\pm}NO_3$
3) [Cu (4,7diphenyl)1,10-phenanthroline) (isoleucinate)]$^{\pm}NO_3$
4) [Cu (4,7diphenyl-1,10-phenanthroline) (leucinate)]$^{\pm}NO_3$
5) [Cu (4,7diphenyl-1,10-phenanthroline) (serinate)]$^{\pm NO}{}_3$
6) [Cu (4,7diphenyl-1,10-phenanthroline) (valinate)]$^{\pm}NO_3$

DETAILED DESCRIPTION OF THE INVENTION

This invention refers to a process to obtain new mixed copper aminoacidate complexes from phenylate phenanthrolines to be used as anticancerigenic agents in which Cu $(NO_3)_2$. $5H_2O$ is used as raw material; this complex has not been used in conventional process; the technique makes it possible to obtain crystals that are highly soluble in water and furthermore the reactions that occur during the process of this invention take place at room temperature thus avoiding the therapeutic properties of the aminoacidate obtained breaking down.

The process generally takes place in two stages according to the following:

1) To form the intermediary copper complex of the [Cu (N-N)]$^{\pm}NO_3$ type, an aqueo-ethanolic solution is prepared with a content of 30%–35% in weight of $Cu(NO_3)_2$. $5H_2O$ and an aqueo-ethanolic solution of 50%–55% in weight of the corresponding diimine; both are immediately brought into contact in a reactor for approximately 5 minutes at room temperature. The resulting pH must be between 5 and 7.

2) To form the stabilized copper complex (monodiimine aminoacidate nitrate), an aqueous solution is added to the above mentioned components 10%–15% in wight of the minoacidate ion (N-O) adjusting the slightly alkaline pH with an aqueous aquoammoniacal solution.

The process is also characterized because it is passed through a millipore filter in order to eliminate raw materials and secondary products, to sterilize the solution and to obtain a pure product precipitates and is finally filtered, thus giving a yield of 60%; to achieve greater purity it is recrystallized in ethanol/water (to a ratio of 30/70). The crystals are royal blue in color.

The complexes formed as a result of this process are any of the following:

1) [Cu (4,7diphenyl-1,10-phenanthroline) (alaninate)]$^{\pm}NO_3$

2) [Cu (4,7diphenyl-1,10-phenanthroline) (glycinate)]$^{\pm}NO_3$

3) [Cu (4,7diphenyl)1,10-phenanthroline) (isoleucinate)]$^{\pm}NO_3$

4) [Cu (4,7diphenyl-1,10-phenanthroline) (leucinate)]$^{\pm}NO_3$

5) [Cu (4,7diphenyl-1,10-phenanthroline) (serinate)]$^{\pm}NO_3$

6) [Cu (4,7diphenyl)1,10-phenanthroline) (valinate)]$^{\pm}NO_3$

Examples of the invention are described below in order to illustrate it better, not with the purposes of restricting its scope.

EXAMPLE 1

To obtain a complex with the formula [Cu (4,7-diphenyl-1,10-phenanthroline) (alaninate)$^{\pm}NO_3$, a first aqueo-ethanolic solution was prepared in a container with 215.6 mg. of Cu $(NO_3)_2$. $5H_2O$; a second aqueo-ethanolic solution was immediately prepared with 332 mg of 4,7-diphenyl-1,10-phenanthroline; the aqueous solutions were then made to react in a reactor at room temperature; soon afterwards a regulating agent was added to stabilize the intermediary complex obtained, keeping the pH between 5 and 7, an aqueous solution with 105.6 mg of alaline was subsequently added to the intermediary complex obtained; the reaction was kept at a pH of between 7 and 8 and regulated with an aqueo-ammonical solution for five minutes; the product obtained was immediately passed through a millipore filter; it was concentrated by slightly heating and distilled in vacuum until the volume was reduced by half; once cooled the mixture of the aromatic complex obtained from copper alaninate was precipitated; it was then filtered and recrystallized in an ethanol/water mixture (with a ratio of 30/70). The crystals obtained were royal were royal blue in color and their characterization was the following:

COMPOUND FORMULA: [Cu (4,7-diphenyl-1,10-phenanthroline) (alaninate)]$^{\pm}NO_3$.

ELEMENT ANALYSIS OBTAINED (%): 59.36 C; 4.1 H; 10.21 N.

CALCULATED ELEMENT ANALYSIS (%): (59.39) C; (4.032) H; (10.26) N.

BORN MAGNETONS (μ, eff): 2.28.

CONDUCTIVITY (Ohms.mol.cm$^{-1}$); 133 (water).

λmax visible (nm): 611.

STRUCTURE (R): 0.064.

IR (cm$^{-1}$): 1610, 1430, 1380, 1289, 1170, 1020, 930, 855, 840, 740, 670, 635.

(IR=infrared analysis.

EXAMPLE 2

A complex with the formula [Cu (4,7-diphenyl-1,10-phenanthroline) (glycinate)]$^{\pm}NO_3$ was obtained by preparing an aqueo-ethanolic solution in a container with 215.6 mg of Cu $(NO_3)_2 5H_2O$: and also preparing an aqueo-ethanolic solution with 332 mg of 4,7-diphenyl-1,10-phenanthroline; these aqueous solutions were then made to react in a reactor at room temperature; shortly afterwards a regulating agent was added to stabilize the intermediary complex obtained with the formula [Cu (4,7-diphenyl-1,10-phenanthroline)] $^{\pm}NO_3$, keeping the pH between 5 and 7; an aqueous solution with 105.6 mg of glycine was subsequently added to the intermediary complex obtained; the reaction was kept at a pH of between 7 and 8 and regulated with an aqueo-ammonical solution for 5 minutes; the product obtained was immediately passed through a millipore filter; it was concentrated by slight heating and distilled in vacuum until the volume was reduced by half; when the mixture had cooled, the aromatic complex based on copper glycinate was precipitated; it was then filtered and recrystallized in an ethanol/water mixture (at ratio of 30/70). The crystals obtained were royal were royal blue in color and their characterization was the following:

COMPOUND FORMULA : [Cu (4,7-diphenyl-1,10-phenanthroline) (glycinate)]$^{\pm}NO_3$.

ELEMENT ANALYSIS OBTAINED (%): 58.63 C; 3.8 H; 10.51 N.

CALCULATED ELEMENT ANALYSIS (%): (58.70) C; (3.79) H; (10.53) N.

BORN MAGNETONS (μ, eff): 1.75.

CONDUCTIVITY (Ohms.mol.cm$^{-1}$); (35 ethanol).

λmax visible (nm): 617.

IR (cm$^{-1}$): 1610, 1450, 1380, 1250, 1175, 865, 750, 640.

EXAMPLE 3

A complex with the formula [Cu (4,7-diphenyl-1,10-phananthroline) (isoleucinate)]$^{\pm}NO_3$ was obtained following the technique descried in examples 1 and 2 to obtain the intermediary complex with the formula [Cu (4,7-diphenyl-1,10-phenanthroline)]$^{\pm}NO_3$ which was stabilized with a regulating agent to keep pH between 5 and 7; an aqueous solution was then added with 156 mg of isoleucine; the reaction was kept at a pH of between 7 and 8 and regulated with an aqueo-ammonical solution for 5 minutes; the product obtained was immediately passed through a millipore filter; it was concentrated with slight heating and distilled in vacuum until the volume was reduced by half; when the mixture had cooled, the aromatic complex based on copper isoleucinate was precipitated; it was filtered and recrystallized in an ethanol/water (at a ratio of 30/70). The crystals obtained were royal were royal blue in color and their characterization was the following:

COMPOUND FORMULA : [Cu (4,7-diphenyl-1,10-phenanthroline) (isoleucinatenate)]$^{\pm}NO_3$.

ELEMENT ANALYSIS OBTAINED (%): 60.89 C; 4.9 H; 9.4 N.

CALCULATED ELEMENT ANALYSIS (%): (61.27) C; (4.8) H; (9.53) N.

BORN MAGNETONS (μ, eff): 1.75.

CONDUCTIVITY (Ohms.mol.cm$^{-1}$); 21.2 (ethanol).

Ir (cm$^{-1}$): 1607, 1385, 1234, 1176, 1100, 854, 837, 769, 738, 707, 673, 634, 576.

EXAMPLE 4

A complex with the formula [Cu (4,7-diphenyl-1,10-phenanthroline) (leucinate)]$^{\pm}NO_3$ was obtained following the technique described in examples 1 and 2 to obtain the intermediary complex with the formula [Cu (4,7-diphenyl-1,10-phenanthroline)]$^{\pm}NO_3$ which was stabilized with a regulating agent to keep the pH between 5 and 7; an aqueous solution was then added with 156 mg of leucine; the reaction was regulated at a pH of between 7 and 8 with an aqueo-ammonical solution for 5 minutes; the product obtained was immediately passed through a millipore filter; it was concentrated by slight heating and distilled in vacuum until the volume was reduced by half; when the mixture cooled, the aromatic complex based on copper leucinate was precipitated; it was filtered and recrystalized in an ethanol/water (ratio: 30/70).

The crystals obtained were royal were royal blue in color and their characterization was the following:

COMPOUND FORMULA : [Cu (4,7-diphenyl-1,10-phenanthroline) (leucinate)]$^{\pm}NO_3$.

ELEMENT ANALYSIS OBTAINED (%): 61.3 C; 4.85 H; 9.5 N.

CALCULATED ELEMENT ANALYSIS (%): (61.27) C; (4.80) H; (9.53) N.

BORN MAGNETONS (μ, eff): 1.82.

CONDUCTIVITY (Ohms.mol.cm$^{-1}$); 21.9 (ethanol).

λmax visible (nm): 608.

IR (cm$^{-1}$): 1651, 1566, 1380, 1237, 1115, 934, 853, 835, 738, 669, 635.

EXAMPLE 5

A complex with the formula [Cu (4,7-diphenyl-1,10-phenanthroline) (serinate)]$^{\pm}NO_3$ was obtained; the intermediary complex was prepared with the formula [Cu (4,7-diphenyl-1,10-phenanthroline)]$^{\pm}NO_3$ by means of the technique described in examples 1 and 2 and its pH was regulated at between 5 and 7; an aqueous solution was then added with 124.8 mg of serine; the reaction was regulated with a pH of between 7 and 8 with an aqueo-ammonical soluton for 5 minutes; it was immediately passed through a millipore filter; it was concentrated by slight heating and distilled in vacuum until the volume was reduced by half; when the mixture cooled, the aromatic complex based on copper serinate was precipitated; it was filtered and recrystallized in ethanol/water (ratio: 30/70).

The crystals obtained were royal were royal blue in color and their characterization was the following:

COMPOUND FORMULA : [Cu (4,7-diphenyl-1,10-phenanthroline) (serinate)]$^{\pm}NO_3$.

ELEMENT ANALYSIS OBTAINED (%): 57.67 C; 3.98 H; 9.97 N.

CALCULATED ELEMENT ANALYSIS (%): (57.70)O; (3.95) H; (9.95) N.

BORN MAGNETONS (μ, eff): 1.79.

CONDUCTIVITY (Ohms.mol.cm$^{-1}$); 26.3 (ethanol).

λmax visible (nm): 605.

IR (cm$^{-1}$): 1610, 1380, 1245, 1155, 1050, 855, 730, 630.

EXAMPLE 6

A complex with the formula [Cu (4,7-diphenyl-1,10-phenanthroline) (valinate)]$^{\pm}NO_3$ was obtained, the intermediary complex was prepared with the formula [Cu (4,7-diphenyl-1,10-phenanthroline)]$^{\pm}NO_3$ following the technique described in examples 1 and 2 and its pH was regulated at between 5 and 7; an aqueous solution with 139.2 mg of valine was then added and the reaction regulated with a pH of between 7 and 8 and with an aqueo-ammonical solution for 5 minutes; the product obtained was immediately passed through a millipore filter; it was concentrated by slight heating and distilled in vacuum until the volume was reduced by half; when the mixture cooled, the aromatic complex based on copper valinate was precipitated; it was filtered and recrystallized in ethanol/water (ratio: 30/70).

The crystals obtained were royal were royal blue in color and their characterization was the following:

COMPOUND FORMULA: [Cu (4,7-diphenyl-1,10-phenanthroline) (valinate)]$^{\pm}NO_3$.

ELEMENT ANALYSIS OBTAINED (%): 60.7 C; 4.59 H; 9.78 N.

CALCULATED ELEMENT ANALYSIS (%): (60.67) C; (4.57) H; 9.76) N.

BORN MAGNETONS (μ, eff): 1.8.

CONDUCTIVITY (Ohms.mol.cm$^{-1}$); 19 (ethanol).

λmax visible (nm); 610.

IR (cm$^{-1}$): 1620, 1380, 716, 666.

The complexes obtained as a result of this process have a biological activity as anticancerigenic agents preferably for therapeutic use in the treatment of solid and liquid cancerous tumors such as leukemia.

A description is given below of an example of the cytotoxicity and biological activity of one of the complexes with the purpose of showing the complex's pharmacological capacity. Each of the other complexes obtained has the same or a similar pharmacological capacity.

An example of the biological activity of [Cu (4,7-diphenyl-1,10-phenanthroline) (glicinate)]$^{\pm}NO_3$:

Two tests were performed. The first was carried out "in vitro" and in this test, an experiment was done with a cell line of the cytotoxicity the new complex provokes using two conventional reagents, cys-platinum and mitomycine, as points of reference. In the second test, "in vitro", the biological activity of this new complex was quantified in mice suffering from leukemia (a liquid cancerous tumor).

"IN VITRO" TEST

1) The cell line x63 (murine myeloma) was treated with different molar concentrations of the two drugs conventionally used in the treatment of cancerous tumors: mitomycine and cysplatimum. Then, the percent of cell survival were quantified using a conventional test consisting in measuring the incorporation of thymidyne tritiated ($^3$H-tdR) into the cells with murine myeloma that were resistant to treatment, since this percentage is directly proportional to the number of living malignant cells.

Table I show the different molar concentrations of the drugs applied to the malignant cell line (murine myeloma) and their respective effects. The cell line x63 showed a greater percentage of survival when treated with cys-platinum.

Table II compare cytoxicity provoked by the new copper aminoacidate complex [Cu (4,7-diphenyl-1,10-phehanthroline) (glycinate)]$^{\pm}NO_3$ with respect to the conventional cys-platinum drug. The different molar concentrations and their corresponding percentages of survival and above the expected norm are shown. The two effects measured are compared with the reagents that form part of the new copper aminoacidate complex [Cu $NO_3$-4,7-diphenyl-1,10-phenantholine, glycine) used independently without their showing signs of having any biological activity on the malignant cell line and which can thus be used as points of comparison.

TABLE I

DETERMINATION OF THE CYTOTOXICITY OF CYS—PLATINUM AND MITOMYCINE BY THE INCORPORATION OF $^3$H-tdR INTO THE CELL LINE × 63 (MURINE MYELOMA).

| Molar Concentration | Survival % |
|---|---|
| MITOMYCINE | |
| $3.72 \times 10^{-8}$ | 96% |
| $1.57 \times 10^{-7}$ | 55% |
| $1.57 \times 10^{-6}$ | 27% |
| $1.57 \times 10^{-5}$ | 4% |
| CYS—PLATINUM | |
| $8.3 \times 10^{-8}$ | 100% |
| $8.3 \times 10^{-7}$ | 97% |
| $8.3 \times 10^{-6}$ | 54% |
| $8.3 \times 10^{-5}$ | 27% |

TABLE II

DETERMINATION OF THE CITOTOXICITY OF [Cu(4,7-diphenyl-1,10-phenanthroline)(glycinate)]$^{+-}NO_3$. ITS COMPONENTS AND CYS—PLATINUM.

| $CuNO_3$ | | 4,7-difenil-1,10-fenantrolina | | Glicina | |
|---|---|---|---|---|---|
| Molar Concentration | Survival % | Molar Concentration | Survival % | Molar Concentration | Survival % |
| $4 \times 10^{-8}$ | 82% | $4 \times 10^{-8}$ | 105% | $4 \times 10^{-8}$ | 88% |
| $4 \times 10^{-7}$ | 82% | $4 \times 10^{-7}$ | 110% | $4 \times 10^{-7}$ | 90% |
| $4 \times 10^{-6}$ | 84% | $4 \times 10^{-6}$ | 118% | $4 \times 10^{-6}$ | 92% |

| [Cu(4,7-diphenyl-1,10-phenanthroline) (glycinate)]$^{+-}NO_3$ | | Cys—Platinium | |
|---|---|---|---|
| Molar Concentration | Survival % | Molar Concentration | Survival % |
| $4 \times 10^{-8}$ | 88% | $8.2 \times 10^{-8}$ | 100% |
| $4 \times 10^{-7}$ | 95% | $8.2 \times 10^{-7}$ | 89% |
| $4 \times 10^{-6}$ | 54% | $8.2 \times 10^{-6}$ | 48% |
| $4 \times 10^{-8}$ | 95% | $8.3 \times 10^{-8}$ | 100% |
| $4 \times 10^{-7}$ | 98% | $8.3 \times 10^{-7}$ | 90% |
| $4 \times 10^{-6}$ | 8% | $8.3 \times 10^{-6}$ | 8% |

2) The mitotic index (cell reproduction) was measured in human lymphocytes treated with [Cu (4,7-diphenyl-1,10-phehanthroline) (glycinate)]$^{\pm}NO_3$, and it was observed that the greater the molar concentration applied the lower the index of cell reproduction.(See Table III).

TABLE III

MITOTIC INDEX IN HUMAN LYMPHOCYTES TREATED WITH [Cu(4,7-diphenyl-1,10-phenanthroline) (glycinate)]$^{+-}NO_3$.

| Molar Concentration | Mitotic Index |
|---|---|
| 0 | 0.36 |
| $3.25 \times 10^{-7}$ | 0.28 |
| $3.25 \times 10^{-6}$ | 0.22 |
| $3.25 \times 10^{-5}$ | 0.08 |

"IN VITRO" TEST

To carry out this test, female hybrid mice of the $B_6D_2F_1$ strain were used, since this strain is susceptible to $L_{1210}$ lymphoid leukemia (malignant tumorous line). This tumorous line was obtained from UTEP, Texas, U.S.A. where it was typified and a clone isolated of the original $L_{1210}$ line with a stable careotype.

In order to perform the studies of antitumorous substances $1 \times 10^5$ cells/ml of $L_{1210}$ were inoculated intraperitoneally in female mice 10 to 12 weeks old with an average weight of 20 to 22 g.

Experiment 1 negative control: 3 female mice with body weight of 23, 23 and 25 of the $B_6D_2F_1$ strain were chosen and inoculated intra peritoneally with $1 \times 10^5$ cells/ml of $L_{1210}$ malignant tumorous line. These mice were given no chemotherapy.

In order to evaluate the advance of the disease, body weight in grams was recorded each day until the mice died. The results can be seen in Table IV.

TABLE IV

| MICE WITH LEUKEMIA NOT GIVEN CHEMOTHERAPY | | | |
|---|---|---|---|
| | BODY WEIGHT (grams) | | |
| DAYS | MOUSE 1 | MOUSE 2 | MOUSE 3 |
| 0 | 23 | 23 | 25 |
| 1 | 23 | 23 | 25 |
| 2 | 23 | 23 | 24 |
| 3 | 22 | 22 | 23 |
| 4 | 22 | 22 | 23 |
| 5 | 22 | 23 | 24 |
| 6 | 22 | 23 | 24 |
| 7 | 22 | 24 | 24 |
| 8 | 24 | 24 | 25 |
| 9 | 22 | 23 | 23 |
| 10 | 23 | 24 | 24 |
| 11 | 24 | 24 | 24 |
| 12 | 23 | 24 | 24 |
| 13 | 23 | 24 | 24 |
| 14 | 23 | 25 | 25 |
| 15 | DIED | 26 | 27 |
| 16 | — | 26 | 27 |
| 17 | — | DIED | DIED |

Experiment 2: 3 female mice of the $B_6D_2F_1$ strain were chosen with body weight of 21, 22 and 25 grams. They were inoculated intraperitoneally with $1\times10^5$ cells/ml of $L_{1210}$ malignant tumorous line (day 0). In this case chemotherapy treatment was given on days 1, 5 and 9 using a 4 mg/kg/injection of [Cu (4,7-diphenyl-1,10-phenanthroline) (glycinate)]$^{35}$ $NO_3$. In order to assess the evoluation of the disease with the treatment, body weight in grams was recorded each day until the mice died. The results can be seen in Table V.

TABLE V

| Mice with leukemia given a treatment consisting of 4 mg/kg/injection of [Cu(4,7-diphenyl-1,10-phenanthroline) (glycinate)]$^{+}NO_3$. | | | |
|---|---|---|---|
| | BODY WEIGHT (grams) | | |
| DAYS | MOUSE 1 | MOUSE 2 | MOUSE 3 |
| 0 | 21 | 22 | 25 |
| 1 | 21 | 22 | 25 |
| 2 | 21 | 22 | 25 |
| 3 | 21 | 22 | 24 |
| 4 | 21 | 22 | 23 |
| 5 | 21 | 22 | 24 |
| 6 | 21 | 22 | 24 |
| 7 | 20 | 24 | 24 |
| 8 | 24 | 24 | 26 |
| 9 | 21 | 21 | 24 |
| 10 | 21 | 24 | 24 |
| 11 | 21 | 24 | 24 |
| 12 | 22 | 24 | 25 |
| 13 | 23 | 25 | 26 |
| 14 | DIED | 26 | 29 |
| 15 | — | 25 | 27 |
| 16 | — | 26 | 28 |
| 17 | — | 26 | DIED |
| 18 | — | 26 | — |
| 19 | — | DIED | — |

Experiment 3: 3 female mice of the $B_6D_2F_1$ strain with body weight of 18, 22 and 21 grams were selected and inoculated intraperitoneally with $1\times10^5$ cells/ml of the LPV121OPV malignant tumorous line (day 0).

These mice were given chemotherapy treatment on days 1, 5 and 9 but now using a 6 mg/kg/injection of [Cu (4,7diphenyl-1,10-phenanthroline) (glycinate)]$^{+}NO_3$. In order to evaluate the effect of the treatment, a daily recording was made of body weight in grams until the mice died or until a maximum of 50 days had passed (after this time the mice were considered to be free of the effect of the malignant tumor, that is healthy). The results obtained can be seen in Table VI in which two mice can be observed to have recovered.

TABLE VI

| MICE WITH LEUKEMIA GIVEN A TREATMENT CONSISTING OF 6 mg/kg/INJECTION OF [Cu(4,7-diphenyl-1,10-fenanthroline)(glycinate)]$^{+}NO_3$ | | | |
|---|---|---|---|
| | BODY WEIGHT (grams) | | |
| DAYS | MOUSE 1 | MOUSE 2 | MOUSE 3 |
| 0 | 18 | 21 | 21 |
| 1 | 18 | 21 | 21 |
| 2 | 18 | 18 | DIED |
| 3 | 18 | — | |
| 4 | 18 | 18 | — |
| 5 | 20 | 20 | — |
| 6 | 19 | 19 | — |
| 7 | 21 | 22 | — |
| 8 | 23 | 24 | — |
| 9 | 20 | 21 | — |
| 10 | 20 | 21 | — |
| 11 | 21 | 21 | — |
| 12 | 21 | 22 | — |
| 13 | 23 | 25 | — |
| 14 | 23 | 25 | DIED |
| 15 | 25 | 26 | — |
| 16 | 24 | 25 | — |
| 17 | 23 | 22 | — |
| 18 | 22 | 23 | — |
| 19 | 22 | 23 | — |
| 20 | 22 | 23 | — |
| 21 | 22 | 24 | — |
| 22 | 22 | 24 | — |
| 23 | 22 | 24 | — |
| 24 | 22 | 24 | — |
| 25 | 22 | 24 | — |
| 26 | 22 | 24 | — |
| 27 | 22 | 24 | — |
| 28 | 22 | 24 | — |
| 30 | 22 | 24 | — |
| 31 | 22 | 24 | — |
| 32 | 22 | 24 | — |
| 33 | 22 | 24 | — |
| 34 | 22 | 24 | — |
| 35 | 23 | 24 | — |
| 36 | 22 | 24 | — |
| 37 | 22 | 24 | — |
| 38 | 22 | 24 | — |
| 39 | 22 | 24 | — |
| 40 | 23 | 24 | — |
| 41 | 23 | 24 | — |
| 42 | 23 | 24 | — |
| 43 | 23 | 24 | — |
| 44 | 23 | 24 | — |
| 45 | 23 | 24 | — |
| 46 | 24 | 25 | — |
| 47 | 24 | 25 | — |
| 48 | 24 | 25 | — |
| 49 | 25 | 26 | — |
| 50 | 25 | 26 | — |

What is claimed is:

1. A process for preparing an aromatic copper aminoacidate complex from a phenylate phenanthroline useful as an anticancerigenic agent and having the formula [Cu (N-N) (N-O)]$^{+}NO_3$, where the N-N ligand is a diimine compound comprising 4,7-diphenyl-1,10-phenanthroline and the N-O ligand is an aminoacidate ion selected from the group consisting of glycinate, alaninate, isoleucinate, leucinate, serinate, and valinate, comprising the steps of preparing a first aqueous solution containing from 30% to 35% by weight of Cu $(NO_3)_2.5H_2O$, preparing a second aqueo-ethanolic solution containing from 50% to 55% by weight of the diimine compound, combining the first and second aqueous solutions together in a reactor at room temperature to form a reaction medium and obtain a copper complex of the diimine compound while maintaining an acid pH of between 5 and 7, adding to the medium an aqueous solution containing from 10% to 15% by weight of the aminoacidate ion, and thereafter keeping the reaction medium slightly alkaline to obtain an aromatic copper aminoacidate complex selected from the group consisting of:

[Cu (4,7diphenyl-1,10-phenanthroline) (alaninate)]$^{\pm}NO_3$;

[Cu (4,7diphenyl-1,10-phenanthroline) (glycinate)]$^{\pm}NO_3$;

[Cu (4,7diphenyl-1,10-phenanthroline) (isoleucinate)]$^{\pm}NO_3$;

[Cu (4,7diphenyl-1,10-phenanthroline) (leucinate)]$^{\pm}NO_3$;

[Cu (4,7diphenyl-1,10-phenanthroline) (serinate)]$^{\pm}NO_3$; and

[Cu (4,7diphenyl-1,10-phenanthroline) (valinate)]$^{\pm}NO_3$.

2. The process of claim 1, wherein the copper complex of the diimine compound is of the [Cu (N-N)]$^{\pm}NO_3$ type, the first and second solutions being brought into contact in the reactor for approximately 5 minutes at room temperature to yield said copper complex.

3. The process of claim 1, wherein the aqueous solution contains from 12% to 15% by weight of the aminoacidate ion and the reaction medium is kept slightly alkaline after addition of the aminoacidate ion containing aqueous solution with an aqueous-ammonical solution.

4. The process of claim 1, 2, or 3, wherein the aromatic copper aminoacidate complex obtained is passed through a millipore filter, slightly heated and distilled in vacuum to eliminate raw materials and secondary products, and then sterilized to obtain a pure complex.

5. A process for treating a subject suffering from liquid or solid cancerigenic tumors which comprises administering to said subject a therapeutic effective amount of one or more of said aromatic copper aminoacidate complexes produced by the process of claim 1, 2 or 3.

*6. A copper amino acidate diimine nitrate compound selected from the group consisting of:*

*[Cu (4,7diphenyl-1,10-phenanthroline) (alaninate)]$NO_3$;*

*[Cu (4,7diphenyl-1,10-phenanthroline) (glycinate)]$NO_3$;*

*[Cu (4,7diphenyl-1,10-phenanthroline) (isoleucinate)] $NO_3$;*

*[Cu (4,7diphenyl-1,10-phenanthroline) (leucinate)]$NO_3$;*

*[Cu (4,7diphenyl-1,10-phenanthroline) (serinate)]$NO_3$; and*

*[Cu (4,7diphenyl-1,10-phenanthroline) (valinate)]$NO_3$.*

*7. A composition for the treatment of liquid and solid cancerigenic tumors comprising an effective amount of at least one copper amino acidate diimine nitrate compound of claim 6 and acceptable carrier.*

* * * * *